Figure 1:
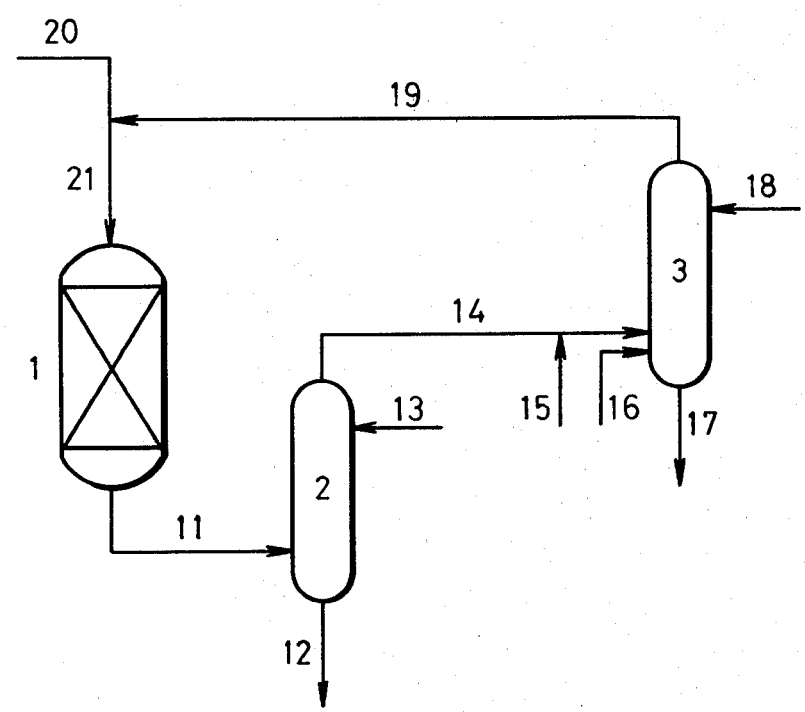

United States Patent [19]

Tahara et al.

[11] Patent Number: 4,461,909
[45] Date of Patent: Jul. 24, 1984

[54] PROCESS FOR CONTINUOUSLY PREPARING A DIESTER OF OXALIC ACID

[75] Inventors: Susumu Tahara; Kozo Fujii; Keigo Nishihira; Masaoki Matsuda; Katsuhiko Mizutare, all of Ube, Japan

[73] Assignee: Ube Industries, Ltd., Ube, Japan

[21] Appl. No.: 495,459

[22] Filed: May 19, 1983

Related U.S. Application Data

[63] Continuation of Ser. No. 293,703, Aug. 17, 1981, abandoned.

[30] Foreign Application Priority Data

Aug. 26, 1980 [JP] Japan ............................ 55-116456
Aug. 26, 1980 [JP] Japan ............................ 55-116458

[51] Int. Cl.$^3$ ............................................ C07C 69/34
[52] U.S. Cl. ................................ 560/193; 560/190; 560/204
[58] Field of Search ........................ 560/204, 190, 193

[56] References Cited

U.S. PATENT DOCUMENTS 4,229,589 10/1980 Nishimura et al. ............... 560/204
4,229,591 10/1980 Nishimura et al. ............... 560/204

FOREIGN PATENT DOCUMENTS 2025950 1/1980 United Kingdom ............... 560/204

*Primary Examiner*—Alan Siegel
*Attorney, Agent, or Firm*—Frishauf, Holtz, Goodman & Woodward

[57] ABSTRACT

There is provided a process for the continuous preparation of a diester of oxalic acid which comprises a first step of reacting carbon monoxide with an ester of nitrous acid in the gaseous phase; a second step of condensing the gaseous reaction mixture to separate a non-condensed gas from a condensed liquid containing the diester of oxalic acid; a third step of introducing the non-condensed gas of the second step to a regeneration column and thereby contacting it with a gas containing molecular oxygen and an alcohol to regenerate nitrogen monoxide in the non-condensed gas into an ester of nitrous acid so as to bring the concentration of nitrogen monoxide in the gas at the outlet of the column to a level of from 2 to 7% by volume; and a fourth step of recycling the gas of the third step containing the ester of nitrous acid and from 2 to 7% by volume of nitrogen monoxide to the reactor of the first step.

18 Claims, 1 Drawing Figure

PROCESS FOR CONTINUOUSLY PREPARING A DIESTER OF OXALIC ACID

This application is a continuation of application Ser. No. 293,703, filed Aug. 17, 1981, abandoned.

The present invention relates to a novel process for preparing a diester of oxalic acid, and particularly to a novel process whereby the production of a diester of oxalic acid is industrially advantageously carried out by a gaseous phase reaction with use of carbon monoxide and an ester of nitrous acid as the starting materials in the presence of a solid catalyst of platinum group metal series.

Diesters of oxalic acid have been used as important starting materials for the syntheses of oxalic acid, oxamide, glycols, intermediates for dyes and pharmaceuticals.

There has hitherto been known a process for preparing a diester of oxalic acid by contacting carbon monoxide and an ester of nitrous acid with a solid catalyst of platinum group metal series in the gaseous phase. This reaction itself is an extremely good reaction for the preparation of diesters of oxalic acid. However, in order to employ this reaction industrially, it is necessary to have a process whereby the reaction can be conducted continuously as is the case for other chemical reactions.

The present inventors have conducted extensive researches with an aim to establish an industrially advantageous continuous process for the production of diesters of oxalic acid by contacting carbon monoxide and an ester of nitrous acid with a solid catalyst of platinum group metal series in the gaseous phase. As a result, it has been found that it is possible to obtain diesters of oxalic acid industrially extremely advantageously by employing a process which comprises;

(1) a first step of introducing a gas containing carbon monoxide and an ester of nitrous acid into a reactor packed with a solid catalyst carrying a platinum group metal or its salt, and thereby conducting a catalytic reaction in the gaseous phase to obtain a product containing a diester of oxalic acid;

(2) a second step of introducing the product of the first step to a condenser thereby to separate a non-condensed gas containing nitrogen monoxide formed by the catalytic reaction of the first step from a condensed liquid containing the diester of oxalic acid;

(3) a third step of introducing the non-condensed gas of the second step to a regeneration column and thereby contacting it with a gas containing molecular oxygen and an alcohol to regenerate nitrogen monoxide in the non-condensed gas into an ester of nitrous acid so as to bring the concentration of nitrogen monoxide in the gas at the outlet of the column to a level of from 2 to 7% by volume; and (4) a fourth step of recycling the gas of third step containing the ester of nitrous acid and from 2 to 7% by volume of nitrogen monoxide to the reactor of the first step. Thus, a continuous process for the production has been developed.

Now, each step of the present invention will be described.

First Step

A gaseous starting material containing carbon monoxide and an ester of nitrous acid, is introduced into a reactor packed with a solid catalyst of platinum group metal series, and thereby a catalytic reaction is carried out in the gaseous phase.

As the reactor, a single tubular or multi-tubular column packed with a catalyst is useful. The contact time of the gaseous starting material with the solid catalyst of platinum metal series is set to be at most 10 seconds, preferably from 0.2 to 5 seconds.

As the solid catalyst of platinum group metal series, palladium is most useful, but platinum, rhodium, ruthenium, and iridium are also useful. Further, salts of these metals such as nitrates, sulfates, phosphates, halides, acetates, oxalates or benzoates, may be used. These materials are used as carried by an inert carrier such as active carbon, alumina, silica, diatomaceous earth, pumice, zeolite, or Molecular Sieve. The amount to be used, in terms of the platinum group metal, is within a range of from 0.01 to 10% by weight, usually from 0.2 to 2% by weight, relative to the amount of the carrier.

The gaseous starting material, i.e. a gas containing carbon monoxide and an ester of nitrous acid may usually be used in a form diluted with an inert gas such as nitrogen or carbon dioxide.

The ester of nitrous acid may preferably be an ester of a saturated monohydric aliphatic or alicyclic alcohol having from 1 to 8 carbon atoms with nitrous acid. As the alcohol component, there may be mentioned, for instance, an aliphatic alcohol such as methanol, ethanol, n-(and iso-)propanol, n-(iso-, sec- and tert-)butanol, n-(and iso-)amyl alcohol, hexanol, or octanol, and an alicyclic alcohol such as cyclohexanol, or methylcyclohexanol. These alcohols may contain a substituent, such as an alkoxy group, which does not hinder the reaction. Among these, methyl or ethyl nitrite is most preferably used.

It is necessary to carry out this reaction under such conditions that there is no formation of a liquid phase in the reaction zone. The conditions for no formation of a liquid phase in the reaction zone vary depending upon the reaction temperature, the reaction pressure and the kind and concentration of the ester of nitrous acid used, and therefore can not simply be determined.

However, with respect to the reaction temperature, the reaction proceeds in a sufficiently high speed even at a low temperature, and the lower the reaction temperature is, the less side reactions occur. Accordingly, so long as the desired space time yield can be maintained, the reaction is carried out at a relatively low temperature, i.e., usually from 50° to 200° C., preferably from 80° to 150° C. Further, with respect to the reaction pressure, the reaction is carried out usually under a pressure from ambient pressure to 10 kg/cm$^2$ (gauge pressure), preferably from ambient pressure to 5 kg/cm$^2$ (gauge pressure). However, in some cases, the reaction pressure may be slightly lower than ambient pressure.

The concentration of the ester of nitrous acid in the gaseous starting material may be varied over a wide range. However, in order to attain a satisfactory reaction rate, it is necessary to adjust the concentration to be at least 1% by volume, usually from 5 to 30% by volume. The concentration of carbon monoxide in the gaseous starting material may be varied over a wide range, and is usually selected within a range of from 10 to 90% by volume.

Second Step

The product of the first step is led to a condenser, cooled to a temperature at which the diester of oxalic acid in the product is condensed, and separated into a condensed fluid and a non-condensed gas.

The condensed liquid thus separated, contains small amounts of by-products such as a diester of carbonic acid, and an ester of formic acid, in addition to the desired diester of oxalic acid. A refined diester of oxalic acid is obtainable by a simple purification operation such as distillation. On the other hand, the non-condensed gas contains non-reacted carbon monoxide, an ester of nitrous acid and the like, in addition to the nitrogen monoxide formed by the catalytic reaction of the first step. Further, during this step, a part of the desired diester of oxalic acid is carried by the non-condensed gas, and then hydrolized by water formed during the regeneration of nitrogen monoxide in the subsequent third step, and it is possible that the resulting oxalic acid accumulates within the gas recycling system. Furthermore, when the desired product is the one having a relatively high melting point, such as dimethyl oxalate, it is possible that the desired product solidifies and deposits on the wall of the condenser and finally plugs the condenser.

In order to solve these problems, it is possible to employ a method wherein the product of the first step is cooled for condensation at a temperature of at most the boiling point of an alcohol while contacting it with the alcohol. For instance, when the desired product is dimethyl oxalate, it is preferred that the cooling and condensation are carried out at a temperature of from 30° to 60° C. while supplying from 0.01 to 0.1 part by volume of methanol, relative to 100 parts by volume of the reaction mixture to be treated.

Third Step

The non-condensed gas separated in the second step is led to a regeneration column and contacted with a gas containing molecular oxygen and an alcohol thereby to regenerate nitrogen monoxide in the gas into an ester of nitrous acid.

As the regeneration column for this step, a usual gas-liquid contact apparatus such as a packed column, a bubble column, a spray column, or a multi-staged column, may be employed. The alcohol to be used, is selected from alcohol components which may constitute said ester of nitrous acid.

The non-condensed gas to be contacted with the alcohol and the gas containing molecular oxygen, may be introduced into the regeneration column individually or in a mixed state.

In the regeneration column, a part of nitrogen monoxide is oxidized to nitrogen dioxide and at the same time, these substances are allowed to be absorbed and react with the alcohol and thereby to be regenerated as the ester of nitrous acid.

The most important point in this step is to control the concentration of nitrogen monoxide in the gas discharged from the regeneration column to be within a range of from 2 to 7% by volume, and to maintain the gas to contain as little nitrogen dioxide and oxygen as possible, most preferably with substantially no nitrogen dioxide and oxygen. Namely, if the concentration of nitrogen monoxide in the regenerated gas is greater than the above-mentioned upper limit, the reaction rate for the formation of the diester of oxalic acid is remarkably decreased and the yield is lowered, when said gas is recycled for use in the reactor of the first step. On the other hand, if said concentration is lower than the above-mentioned lower limit, the amounts of nitrogen dioxide and oxygen in the regenerated gas will be increased, and they will cause substantial deterioration of the activity of the platinum group metal catalyst of the first step.

Accordingly, it is preferred that from 0.08 to 0.2 mole, in terms of oxygen, of the gas containing molecular oxygen, relative to one mole of nitrogen monoxide in the gas introduced to the regeneration column, is supplied and these gases are contacted with the alcohol at a temperature of at most the boiling point of the alcohol thus used. The contact time is preferably from 0.5 to 20 seconds. Further, the alcohol is used in such an amount as to be sufficient for completely absorbing and reacting the resulting nitrogen dioxide and an almost equimolar amount of nitrogen monoxide, and usually, from 2 to 5 parts by volume of the alcohol is preferably used relative to one part by volume of nitrogen monoxide in the gas introduced into the regeneration column.

Further, since this invention is a continuous process, a loss of a nitrogen component is unavoidable, and its supplementation may be made by supplying the ester of nitrous acid to the reactor of the first step, or by introducing a nitrogen oxide such as nitrogen monoxide, nitrogen dioxide, dinitrogen trioxide or dinitrogen tetroxide, or nitric acid into the regeneration column of the third step.

Further, in case the content of nitrogen monoxide in the non-condensed gas in the second step is great, and if the ester of nitrous acid is obtainable in an excess amount during the regeneration of the nitrogen monoxide into the ester of nitrous acid in the third step, the entire amount of the non-condensed gas needs not be led to the regeneration column and a part thereof may directly be recycled to the reactor of the first step.

The liquid discharged from the regeneration column is an alcohol solution containing water formed as a by-product by the regeneration reaction. This may be refined by an operation such as distillation to such an extent that the water content in the alcohol becomes to be at most 5% by volume, preferably at most 2% by volume, and may then be reused as an alcohol source for the third step, and in a proper case, as an alcohol source for the second step.

Fourth Step

The regenerated gas discharged from the regeneration column of the third step and containing from 2 to 7% by volume of nitrogen monoxide, is recycled to the reactor of the first step.

When the regenerated ester of nitrous acid is an ester of an alcohol having at least 4 carbon atoms, such as n-butyl nitrite, or n-amyl nitrite, it forms an azeotropic mixture with water formed as a by-product by the regeneration reaction and consequently, water is contained in the regenerated gas. Accordingly, if this gas is supplied in that state to the reactor of the first step, the water hinders the reaction for the formation of the diester of oxalic acid. Therefore, it is desirable that water in the gas is removed by an operation such as distillation before the gas is recycled to the reactor. On the other hand, when the regenerated ester of nitrous acid is methyl nitrite, ethyl nitrite, n-propyl nitrite, or i-propyl nitrite, it does not form an azeotropic mixture with water formed as a by-product by the regeneration reaction, and accordingly, the regenerated gas contains no water and may therefore be recycled to the reactor as it is.

Further, this regenerated gas may be mixed with another gaseous starting material, i.e., carbon monoxide, and then the mixture may be recycled to the reactor.

Now, the process of the present invention will be described in detail in accordance with the flow-sheet diagram shown in FIG. 1 illustrating an embodiment of the invention. In the drawing, 1 designates a reactor, 2 designates a condenser, 3 designates a regeneration column and 11 to 21 represent conduits (pipe lines).

A gas containing carbon monoxide, an ester of nitrous acid and nitrogen monoxide is compressed by a gas-recycling device (not shown) and introduced into the top of a multi-tubular reactor 1 having reaction tubes packed with a platinum group metal catalyst via a conduit 21. A catalytic reaction is carried out in the gaseous phase in the reactor 1. The gas formed by the reaction upon passing through the catalyst layer is withdrawn from the bottom and introduced to a condenser 2 via a conduit 11.

In the condenser 2, while being contacted with an alcohol supplied from a conduit 13, the gaseous reaction product is condensed, and the condensed liquid containing mainly the diester of oxalic acid is withdrawn from the bottom via a conduit 12 to the outside of the system, thereby to obtain the diester of oxalic acid. On the other hand, a non-condensed gas containing non-reacted carbon monoxide and the ester of nitrous acid and nitrogen monoxide formed as a by-product, is withdrawn from the top and introduced to the bottom of the regeneration column 3 via a conduit 14.

In the regeneration column 3, the non-condensed gas is countercurrently contacted and reacted with a gas containing molecular oxygen and supplied to the bottom via a conduit 16 and an alcohol supplied to the top via a conduit 18, whereupon an ester of nitrous acid is formed. At the lower portion of the regeneration column 3, the oxidation reaction of nitrogen monoxide to nitrogen dioxide takes place predominantly, and on the other hand, at the top portion, the absorption reaction thereof to the alcohol takes place predominantly. If the nitrogen source for the formation of the ester of nitrous acid is inadequate, a nitrogen oxide may be supplied to the bottom via conduit 15.

The gas containing the ester of nitrous acid formed in the regeneration column 3 (which contains from 2 to 7% by volume of nitrogen monoxide) is recycled to the reactor 1 via conduits 19 and 21 together with carbon monoxide supplied afresh from a conduit 20. On the other hand, the water formed as a by-product in the regeneration column 3 is withdrawn in a form of an aqueous alcohol solution from the bottom via a conduit 17. This aqueous alcohol solution is subjected to an operation such as distillation to remove the water in the liquid, and thereafter may be reused as an alcohol source to be supplied to the regeneration column 3 or the condenser 2 via said conduit 18 or 13.

Now, the invention will be described in detail with reference to Examples and Comparative Examples.

EXAMPLE 1

In the tubes of a stainless multi-tubular reactor, which has 6 tubes having an inside diameter of 36.7 mm and a height of 550 mm, there was packed 3 kg (3 liters) of a γalumina catalyst in a form of pellets having a diameter of 5 mm and a height of 3 mm and carrying 0.5% by weight of palladium.

A gaseous mixture of carbon monoxide and the regenerated gas from the regeneration column mentioned below (pressure: 0.2 kg/cm² (gauge pressure), composition: 22.0% by volume of carbon monoxide, 9.1% by volume of methyl nitrite, 3.1% by volume of nitrogen monoxide, 9.4% by volume of methanol, 8.5% by volume of carbon dioxide and 47.0% by volume of nitrogen) was preheated to about 90° C. by a heat exchanger, and then introduced from the top of this catalyst layer by a diaphragm gas-recycling pump at a rate of 12.0 Nm³/hr., and the temperature of the catalyst layer was maintained at 104° to 117° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and, from the top of the condenser, methanol was introduced at a rate of 5.6 liters/hr., whereby the countercurrent contact was carried out at a temperature of about 35° C. (i.e. 30° C. at the top of the condenser and 40° C. at the bottom of the condenser). From the bottom of the condenser, there was obtained 2.8 kg/hr. of a condensed liquid (composition: 46.6% by weight of dimethyl oxalate, 4.9% by weight of dimethyl carbonate, 0.03% by weight of methyl formate and 48.0% by weight of methanol). On the other hand, from the top of the condenser, 13.6 Nm³/hr. of a non-condensed gas (composition: 15.4% by volume of carbon monoxide, 3.9% by volume of methyl nitrite, 6.8% by volume of nitrogen monoxide, 24.2% by volume of methanol, 7.6% by volume of carbon dioxide and 41.4% by volume of nitrogen) was obtained.

To this non-condensed gas, 140 liters/hr. of oxygen and 9 liters/hr. of nitrogen monoxide were mixed (the molar ratio of oxygen to nitrogen monoxide in the gas being 0.15) and the mixture was led to the bottom of the gas-liquid contact type regeneration column having an inner diameter of 158 mm and a height of 1,400 mm. From the top of the column, methanol (including the methanol recycled from the regeneration column) was supplied at a rate of 40 liters/hr. The countercurrent contact was carried out at a temperature of about 35° C. (i.e., 30° C. at the top of the column and 40° C. at the bottom of the column), whereby nitrogen monoxide in the gas was regenerated into methyl nitrite. To 14.2 Nm³/hr. of the regenerated gas from the regeneration column (composition: 15.4% by volume of carbon monoxide, 8.0% by volume of methyl nitrite, 2.8% by volume of nitrogen monoxide, 24.2% by volume of methanol, 7.6% by volume of carbon dioxide and 41.3% by volume of nitrogen), there was added 550 liters/hr. of carbon monoxide, and the mixture was supplied to and compressed by said gas recycling pump. The discharged gas was cooled to 20° C. to remove condensed methanol, and then led to the reactor.

On the other hand, 1.2 liters/hr. of an aqueous methanol solution containing 20.0% by weight of water, withdrawn from the regeneration column, was subjected to distillation to remove water and then reused as a methanol source for said column.

The initial space time yield of dimethyl oxalate in this Example was 432 g/l.hr. This continuous reaction was continued for 480 hours and no decrease in the space time yield of dimethyl oxalate was observed.

EXAMPLE 2 AND COMPARATIVE EXAMPLES 1 AND 2

Into the gas supplied to the regeneration column, oxygen was introduced in a molar ratio to nitrogen monoxide, of 0.094 in Example 2, 0.27 in Comparative Example 1 and 0.051 in Comparative Example 2, and the gas compositions at various portions were maintained as shown in the following table. The production of dimethyl oxalate was continuously carried out with other conditions being the same as those of Example 1.

In the following table, the gas composition of Example 1 is also shown.

TABLE 1

| | Portions | Compositions of gases (% by volume) | | | | | | | |
|---|---|---|---|---|---|---|---|---|---|
| | | CO | $CH_3ONO$ | NO | $O_2$ | $CH_3OH$ | $CO_2$ | $N_2$ | Others |
| Example 1 | Reactor inlet: I | 22.0 | 9.1 | 3.1 | 0 | 9.4 | 8.5 | 47.0 | 0.9 |
| | Reactor outlet: II | 17.8 | 4.6 | 7.9 | 0 | 9.6 | 8.8 | 47.9 | 3.4 |
| | Condenser outlet: III | 15.4 | 3.9 | 6.8 | 0 | 24.2 | 7.6 | 41.4 | 0.7 |
| | Regeneration column inlet: IV | 15.3 | 3.9 | 6.8 | 1.0 | 24.2 | 7.6 | 40.9 | 0.3 |
| | Regeneration column outlet: V | 15.4 | 8.0 | 2.8 | 0 | 24.2 | 7.6 | 41.3 | 0.7 |
| Example 2 | I | 21.0 | 9.6 | 6.0 | 0 | 9.5 | 4.8 | 48.1 | 1.0 |
| | II | 17.7 | 6.1 | 9.8 | 0 | 9.7 | 4.9 | 48.9 | 2.9 |
| | III | 15.2 | 5.3 | 8.4 | 0 | 24.2 | 4.2 | 42.1 | 0.6 |
| | IV | 15.1 | 5.2 | 8.3 | 0.8 | 24.2 | 4.2 | 41.8 | 0.4 |
| | V | 15.2 | 8.4 | 5.2 | 0 | 24.2 | 4.2 | 42.0 | 0.8 |
| Comparative Example 1 | I | 23.0 | 9.6 | 1.0 | 0.3 | 9.5 | 13.4 | 42.2 | 1.0 |
| | II | 21.0 | 8.1 | 2.7 | 0.2 | 9.1 | 13.8 | 42.8 | 2.3 |
| | III | 17.8 | 6.8 | 2.3 | 0.1 | 24.2 | 11.7 | 36.3 | 0.8 |
| | IV | 17.8 | 6.8 | 2.3 | 0.5 | 24.2 | 11.6 | 36.1 | 0.7 |
| | V | 17.8 | 8.2 | 0.9 | 0.3 | 24.2 | 11.7 | 36.2 | 0.7 |
| Comparative Example 2 | I | 21.5 | 9.7 | 9.0 | 0 | 9.5 | 4.2 | 45.1 | 1.0 |
| | II | 19.5 | 7.5 | 11.4 | 0 | 9.6 | 4.3 | 45.6 | 2.1 |
| | III | 16.6 | 6.4 | 9.7 | 0 | 24.2 | 3.6 | 38.7 | 0.8 |
| | IV | 16.5 | 6.4 | 9.7 | 0.5 | 24.1 | 3.6 | 38.7 | 0.5 |
| | V | 16.6 | 8.3 | 7.7 | 0 | 24.2 | 3.6 | 38.9 | 0.7 |

As a result, the initial space time yield of dimethyl oxalate in Example 2 was 340 g/l.hr. and no decrease in the space time yield was observed even after 340 hours.

Whereas, in Comparative Example 1, the initial space time yield of dimethyl oxalate was found to be 207 g/l.hr., but the yield decreased to 145 g/l.hr. after 24 hours and to 105 g/l.hr. after 36 hours. Further, in Comparative Example 2, the initial space time yield of dimethyl oxalate was low at 216 g/l.hr. and the yield further decreased to 184 g/l.hr. after 48 hours.

EXAMPLE 3

In the tubes of a stainless multi-tubular reactor, which has 6 tubes having an inside diameter of 36.7 mm and a height of 550 mm, there was packed 3 kg (3 liters) of a γ-alumina catalyst in a form of pellets having a diameter of 5 mm and a height of 3 mm and carrying 0.5% by weight of palladium.

A gaseous starting material compressed under a pressure of 2.0 kg/cm$^2$ (gauge pressure) (composition: 20.2% by volume of carbon monoxide, 14.9% by volume of methyl nitrite, 3.0% by volume of nitrogen monoxide, 12.7% by volume of methanol, 2.0% by volume of carbon dioxide and 46.2% by volume of nitrogen) was preheated to about 90° C. by a heat exchanger, and then introduced from the top of this catalyst layer by a diaphragm gas-recycling pump at a rate of 6.0 Nm$^3$/hr., and the temperature of the central portion of the catalyst layer was maintained to be about 110° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and from the top of the condenser, methanol was introduced at a rate of 1.5 liters/hr., whereby the countercurrent contact was carried out at a temperature of 40° C. at the top and 43° C. at the bottom. From the bottom of the condenser, there was obtained 2.46 kg/hr. of a condensed liquid (composition: 48.0% by weight of dimethyl oxalate, 1.7% by weight of dimethyl carbonate, 0.04% by weight of methyl oxalate and 47.8% by weight of methanol). On the other hand, from the top of the condenser, 5.5 Nm$^3$/hr. of a non-condensed gas (composition: 13.3% by volume of carbon monoxide, 7.3% by volume of methyl nitrite, 11.9% by volume of nitrogen monoxide, 13.8% by volume of methanol, 2.4% by volume of carbon dioxide and 50.2% by volume of nitrogen) was obtained.

To this non-condensed gas, 119.0 liters/hr. of oxygen and 14.0 liters/hr. of nitrogen monoxide were mixed (the molar ratio of oxygen to nitrogen monoxide in the gas being 0.18) and the mixture was led to the bottom of the gas-liquid contact type regeneration column having an inner diameter of 158 mm and a height of 1,400 mm. From the top of the column, methanol was supplied at a rate of 40 liters/hr. (including the methanol recycled from the regeneration column). The countercurrent contact was carried out at a temperature of about 41° C. at the top of the column and 42° C. at the bottom of the column, whereby nitrogen monoxide in the gas was regenerated into methyl nitrite. The regenerated gas from the regeneration column (composition: 13.3% by volume of carbon monoxide, 15.9% by volume of methyl nitrite, 3.5% by volume of nitrogen monoxide, 14.0% by volume of methanol, 2.4% by volume of carbon dioxide and 49.9% by volume of nitrogen) was supplied to and compressed by said gas recycling pump at a rate of 5.55 Nm$^3$/hr. To 5.15 Nm$^3$/hr. of the discharged gas, there was added 0.85 Nm$^3$/hr. of a gaseous mixture containing 62.6% by volume of carbon monoxide, 9.2% by volume of methyl nitrite, 4.7% by volume of methanol and 23.4% by volume of nitrogen, and the mixture was led to the reactor.

On the other hand, 1.3 liters/hr. of a methanol solution containing 18.0% by weight of water, withdrawn from the regeneration column, was subjected to distillation to remove water and then reused as a methanol source for said column.

The initial space time yield of dimethyl oxalate in this Example was 393 g/l.hr. This continuous reaction was continued for 480 hours and no decrease in the space time yield of dimethyl oxalate was observed.

EXAMPLE 4

In the tubes of a stainless multi-tubular reactor, which has 8 tubes having an inside diameter of 28.0 mm and a height of 1,000 mm, there was packed 3.85 kg (3.85 liters) of a γ-alumina catalyst in a form of pellets having a diameter of 5 mm and a height of 3 mm and carrying 0.5% by weight of palladium.

A gaseous mixture (composition: 20.0% by volume of carbon monoxide, 7.0% by volume of ethyl nitrite, 3.0% by volume of nitrogen monoxide, 6.0% by volume of ethanol, 3.2% by volume of carbon dioxide and 59.8% by volume of nitrogen) compressed under a pressure of 1.8 kg/cm$^2$ (gauge pressure) by a diaphragm gas-recycling pump was preheated to about 90° C. by a heat exchanger and then introduced from the top of the catalyst layer at a rate of 23.0 Nm$^3$/hr., and the temperature of the central portion of the catalyst layer was maintained to be about 110° C. by circulating hot water to the shell side of the reactor.

The gas passed through the catalyst layer was led to the bottom of a Rasching ring packed condenser of gas-liquid contact type having an inside diameter of 158 mm and a height of 1,400 mm, and from the top of the condenser, ethanol was introduced at a rate of 1.8 liters/hr., whereby the countercurrent contact was carried out at a temperature of 40° C. at the top and 43° C. at the bottom. From the bottom of the condenser, there was obtained 2.7 kg/hr. of a condensed liquid (composition: 51.1% by weight of diethyl oxalate, 1.8% by weight of diethyl carbonate, 0.3% by weight of ethyl formate and 38.9% by weight of ethanol). On the other hand, from the top of the condenser 22.6 Nm$^3$/hr. of a non-condensed gas (composition: 18.4% by volume of carbon monoxide, 5.1% by volume of ethyl nitrite, 5.0% by volume of nitrogen monoxide, 6.1% by volume of ethanol, 3.3% by volume of carbon dioxide and 60.8% by volume of nitrogen) was obtained.

To this non-condensed gas, 118.5 Nl/hr. of oxygen was mixed (the molar ratio of oxygen to nitrogen monoxide in the gaseous mixture being 0.104) and the mixture was led to the bottom of the gas-liquid contact type regeneration column having an inner diameter of 158 mm and a height of 1,400 mm. From the top of the column, ethanol was supplied at a rate of 4.2 liters/hr. The countercurrent contact was carried out at a temperature of 40° C. at the top of the column and 42° C. at the bottom of the column, whereby nitrogen monoxide in the gas was regenerated into ethyl nitrite. The regenerated gas from the regeneration column (composition: 18.4% by volume of carbon monoxide, 7.1% by volume of ethyl nitrite, 3.1% by volume of nitrogen monoxide, 6.2% by volume of ethanol, 3.3% by volume of carbon dioxide and 60.9% by volume of nitrogen), was supplied to and compressed by said gas recycling pump at a rate of 22.6 Nm$^3$/hr. To 22.3 Nm$^3$/hr. of the discharged gas, there was added 0.7 Nm$^3$/hr. of a gaseous mixture containing 71.5% by volume of carbon monoxide, 4.4% by volume of ethyl nitrite, 0.6% by volume of ethanol, and 23.6% by volume of nitrogen, and the mixture was led to the reactor.

On the other hand, 4.1 liters/hr. of an ethanol solution containing 9.2% by weight of water, withdrawn from the regeneration column, was subjected to dehydration and then reused as an ethanol source for said column.

The initial space time yield of diethyl oxalate in this Example was 355 g/l.hr. This continuous reaction was continued for 480 hours and little decrease in the space time yield of diethyl oxalate was observed.

We claim:

1. A process for continuously preparing a diester of oxalic acid, which comprises
   (1) a first step of passing gas containing carbon monoxide and an ester of a saturated monohydric aliphatic or alicyclic alcohol having 1 to 8 carbon atoms with nitrous acid into a reactor packed with a solid catalyst comprising a platinum group metal or its salt, and catalytically reacting said carbon monoxide and ester of nitrous acid in the gaseous phase at a temperature of from 50° to 200° C. and a pressure of from ambient pressure to 10 kg/cm$^2$ (guage) to obtain a product containing a diester of oxalic acid;
   (2) a second step of passing the product of the first step to a condenser to separate said product into a non-condensed gas containing nitrogen monoxide formed by the catalytic reaction of the first step from a condensed liquid containing the diester of oxalic acid;
   (3) a third step of passing the non-condensed gas of the second step to a regeneration column and therein contacting it with a gas containing molecular oxygen and an alcohol to react with nitrogen monoxide in the non-condensed gas to regenerate said ester of nitrous acid as a gas and to provide a concentration of nitrogen monoxide in said gas at the outlet of the regeneration column of from 2 to 7% by volume; and
   (4) a fourth step of recycling the outlet gas of the third step containing the ester of nitrous acid and from 2 to 7% by volume of nitrogen monoxide to the reactor of the first step.

2. The process as claimed in claim 1, wherein the amount of said gas containing molecular oxygen in the third step is in the range of 0.08 to 0.2 mole in terms of oxygen relative to one mole of nitrogen monoxide passed into said regeneration column.

3. The process as claimed in claim 1, wherein the amount of the alcohol used in the third step is in the range of 2 to 5 parts by volume relative to one part by volume of nitrogen monoxide passed into said regeneration column.

4. The process as claimed in claim 1, wherein said solid catalyst comprises palladium or a palladium salt.

5. The process as claimed in claim 4, wherein said catalytic reaction is carried out at a temperature of from 80° to 150° C.

6. The process as claimed in claim 1, wherein the product of the first step is contacted with an alcohol in said condenser and is cooled in said condenser at a temperature of at most the boiling point of said alcohol.

7. The process as claimed in claim 6, wherein said alcohol is a lower alcohol having 1 to 4 carbon atoms.

8. The process as claimed in claim 1, wherein (i) the amount of said gas containing molecular oxygen in the third step is in the range of 0.08 to 0.2 mole in terms of oxygen relative to one mole of nitrogen monoxide passed into said regeneration column; (ii) the amount of the alcohol used in the third step is in the range of 2 to 5 parts by volume relative to one part by volume of nitrogen monoxide passed into said regeneration column; and (iii) said ester of nitrous acid is an ester of a saturated monohydric aliphatic or alicyclic alcohol having 1 to 8 carbon atoms with nitrous acid.

9. The process as claimed in claim 8, wherein (i) said solid catalyst comprises palladium or a palladium salt; (ii) said catalytic reaction is carried out at a temperature of from 50° to 200° C.; and (iii) said catalytic reaction is carried out under a pressure of ambient pressure to 10 kg/cm$^2$ (gauge).

10. The process of claim 8, wherein (i) said solid catalyst comprises palladium or a palladium salt; (ii) said catalytic reaction is carried out at a temperature of from 80° to 150° C.; and (iii) said catalytic reaction is carried out under a pressure of ambient pressure to 10 kg/cm$^2$ (gauge).

11. The process as claimed in claim 8, wherein said alcohol is a lower alcohol having 1 to 4 carbon atoms.

12. The process as claimed in claim 9, wherein said alcohol is a lower alcohol having 1 to 4 carbon atoms.

13. The process as claimed in claim 10, wherein said alcohol is a lower alcohol having 1 to 4 carbon atoms.

14. The process as claimed in any of claims 8, 10, 11 or 13, wherein the product of the first step is contacted with an alcohol in said condenser and is cooled in said condenser at a temperature of at most the boiling point of said alcohol.

15. The process as claimed in any one of claims 1, 8, 10, 11 or 13, wherein said ester of nitrous acid is the methyl ester of nitrous acid; said diester of oxalic acid is the dimethyl oxalate; and said alcohol is methyl alcohol.

16. The process as claimed in any one of claims 1, 8, 10, 11 or 13, wherein said ester of nitrous acid is the ethyl ester of nitrous acid; said diester of oxalic acid is the diethyl oxalate; and said alcohol is ethyl alcohol.

17. The process as claimed in claim 14 wherein said gas at the outlet of said regeneration column contains substantially no nitrogen dioxide and no oxygen.

18. The process as claimed in claim 1 wherein said gas at the outlet of said regeneration column contains substantially no nitrogen dioxide and no oxygen.

* * * * *